US006939703B2

(12) United States Patent
Van Der Laan et al.

(10) Patent No.: US 6,939,703 B2
(45) Date of Patent: Sep. 6, 2005

(54) **AMYLOLYTIC ENZYMES DERIVED FROM THE *B.LICHENIFORMIS* α-AMYLASE, HAVING IMPROVED CHARACTERISTICS**

(75) Inventors: Jan M. Van Der Laan, Breda (NL); Wolfgang Aehle, Delft (NL)

(73) Assignee: Genencor International, Inc., Palo Alto, CA (US)

( * ) Notice: Subject to any disclaimer, the term of this patent is extended or adjusted under 35 U.S.C. 154(b) by 0 days.

(21) Appl. No.: 10/199,922

(22) Filed: Jul. 18, 2002

(65) Prior Publication Data

US 2003/0022346 A1 Jan. 30, 2003

Related U.S. Application Data (63) Continuation of application No. 08/981,184, filed on Dec. 11, 1997, now abandoned.

(30) Foreign Application Priority Data

May 2, 1995 (EP) .................................. PCT/EP95/01688

(51) Int. Cl.[7] .............................. C12N 9/28; C12N 9/26; C12N 9/54; C12Q 1/40; C12P 19/14
(52) U.S. Cl. .................... 435/202; 424/93.3; 424/93.46; 424/246.1; 435/22; 435/99; 435/201; 435/202; 435/221; 435/222; 435/252.31; 435/252.2; 536/23.7
(58) Field of Search ............................. 424/93.3, 93.46, 424/246.1; 435/22, 99, 201, 202, 221, 222, 252.31, 252.2, 204, 252.5; 536/23.7; 935/74

(56) References Cited

FOREIGN PATENT DOCUMENTS

| DK | PCT/DK 93/00230 | | 7/1993 | | |
|---|---|---|---|---|---|
| EP | 0414297 | | 10/1996 | | |
| FR | 2676456 | * | 5/1991 | ............ | C12N/9/28 |
| WO | WO 91/00353 | * | 1/1991 | ............ | C12N/15/56 |
| WO | WO 94/02597 | * | 2/1994 | ............ | C12N/9/28 |
| WO | WO 94/18314 | * | 8/1994 | ............ | C12N/9/28 |

OTHER PUBLICATIONS

Brady et al., "Solution of the Structure of *Aspergillus niger* Acid α–Amylase by Combined Molecular Replacement and Multiple Isomorphous Replacement Methods," *Acta Cryst* (1991) B47:527–535.

Ho et al., Site–directed mutagenesis by overlap extension using the polymerase chain reaction, *Gene* (1989) 77, pp. 51–59.

Holm et al., "Random mutagenesis used to probe the structure and function of *Bacillus stearothermophilus* alpha–amylase," *Prot. Engineering* (1990) 3:181–191.

Nagashima et al., "Site–directed Mutagenesis of Catalytic Active–site Residues of Taka–amylase A", *Biosci. Biotech. Biochem.*, 56(2). 207–210, 1992.

Qian et al., "Structure and Molecular Model Refinement of Pig Pancreatic α–Amylase at 2–1 Å Resolution," *J Mol Biol* (1993) 231:785–799.

Sogaard et al., "Site–directed Mutagenesis of Histidine 93, Aspartic Acid 180, Glutamic Acid 205, Hisitidine 290, and Aspartic Acid 291 at the Active Site and Tryptophan 279 at the Raw Starch Binding Site in Barley α–amylase 1," *J Biol Chem* (1993) 268:22480–22484.

(Continued)

*Primary Examiner*—Lynette R. F. Smith
*Assistant Examiner*—J. Hines
(74) *Attorney, Agent, or Firm*—Genencor International, Inc.

(57) ABSTRACT

The present invention relates to novel amylolytic enzymes having improved characteristics for the use in starch degradation, in textile or paper desizing and in household detergent compositions. The disclosed α-amylases show surprisingly improved properties with respect to the activity level and the combination of thermostability and a higher activity level. These improved properties make them more suitable for the use under more acidic or more alkaline conditions. The improved properties allow also the reduction of the Calcium concentration under application conditions without a loss of performance of the enzyme.

22 Claims, 3 Drawing Sheets

OTHER PUBLICATIONS

Stanssens et al., "Efficient oligonucleotide–directed construction of mutations in expression vectors by the gapped duplex DNA method using alternating selectable markers", *Nucl. Acids Res.* 17(12) (1989) pp. 4441–4454.

Swift et al., "Structure and Molecular Model Refinement of *Aspergillus oryzae* (TAKA) α–Amylase: an Application of the Simulated–Annealing Method," *Acta Cryst* (1991) B47:535–544.

Takase, K., "Effect of mutation of an amino acid residue near the catalytic site on the activity of *Bacillus stearothermophilus* α–amylase", *Eur. J. Biochem.*, 211 (1993) 899–902.

Vihinen et al., "Site–Directed Mutagenesis of a Thermostable α–Amylase from *Bacillus stearothermophilus*: Putative Role of Three Conserved Residues," *J Biochem* (1990) 107:267–272.

* cited by examiner

|     |     |     |     | 5   |     |     |     | 10  |     |     |     | 15  |
| --- | --- | --- | --- | --- | --- | --- | --- | --- | --- | --- | --- | --- |
| ALA | ASN | LEU | ASN | GLY | THR | LEU | MET | GLN | TYR | PHE | GLU | TRP | TYR | MET |
|     |     |     |     | 20  |     |     |     | 25  |     |     |     | 30  |
| PRO | ASN | ASP | GLY | GLN | HIS | TRP | LYS | ARG | LEU | GLN | ASN | ASP | SER | ALA |
|     |     |     |     | 35  |     |     |     | 40  |     |     |     | 45  |
| TYR | LEU | ALA | GLU | HIS | GLY | ILE | THR | ALA | VAL | TRP | ILE | PRO | PRO | ALA |
|     |     |     |     | 50  |     |     |     | 55  |     |     |     | 60  |
| TYR | LYS | GLY | THR | SER | GLN | ALA | ASP | VAL | GLY | TYR | GLY | ALA | TYR | ASP |
|     |     |     |     | 65  |     |     |     | 70  |     |     |     | 75  |
| LEU | TYR | ASP | LEU | GLY | GLU | PHE | HIS | GLN | LYS | GLY | THR | VAL | ARG | THR |
|     |     |     |     | 80  |     |     |     | 85  |     |     |     | 90  |
| LYS | TYR | GLY | THR | LYS | GLY | GLU | LEU | GLN | SER | ALA | ILE | LYS | SER | LEU |
|     |     |     |     | 95  |     |     |     | 100 |     |     |     | 105 |
| HIS | SER | ARG | ASP | ILE | ASN | VAL | TYR | GLY | ASP | VAL | VAL | ILE | ASN | HIS |
|     |     |     |     | 110 |     |     |     | 115 |     |     |     | 120 |
| LYS | GLY | GLY | ALA | ASP | ALA | THR | GLU | ASP | VAL | THR | ALA | VAL | GLU | VAL |
|     |     |     |     | 125 |     |     |     | 130 |     |     |     | 135 |
| ASP | PRO | ALA | ASP | ARG | ASN | ARG | VAL | ILE | SER | GLY | GLU | HIS | LEU | ILE |
|     |     |     |     | 140 |     |     |     | 145 |     |     |     | 150 |
| LYS | ALA | TRP | THR | HIS | PHE | HIS | PHE | PRO | GLY | ARG | GLY | SER | THR | TYR |
|     |     |     |     | 155 |     |     |     | 160 |     |     |     | 165 |
| SER | ASP | PHE | LYS | TRP | HIS | TRP | TYR | HIS | PHE | ASP | GLY | THR | ASP | TRP |
|     |     |     |     | 170 |     |     |     | 175 |     |     |     | 180 |
| ASP | GLU | SER | ARG | LYS | LEU | ASN | ARG | ILE | TYR | LYS | PHE | GLN | GLY | LYS |
|     |     |     |     | 185 |     |     |     | 190 |     |     |     | 195 |
| ALA | TRP | ASP | TRP | GLU | VAL | SER | ASN | GLU | ASN | GLY | ASN | TYR | ASP | TYR |
|     |     |     |     | 200 |     |     |     | 205 |     |     |     | 210 |
| LEU | MET | TYR | ALA | ASP | ILE | ASP | TYR | ASP | HIS | PRO | ASP | VAL | ALA | ALA |
|     |     |     |     | 215 |     |     |     | 220 |     |     |     | 225 |
| GLU | ILE | LYS | ARG | TRP | GLY | THR | TRP | TYR | ALA | ASN | GLU | LEU | GLN | LEU |
|     |     |     |     | 230 |     |     |     | 235 |     |     |     | 240 |
| ASP | GLY | PHE | ARG | LEU | ASP | ALA | VAL | LYS | HIS | ILE | LYS | PHE | SER | PHE |
|     |     |     |     | 245 |     |     |     | 250 |     |     |     | 255 |
| LEU | ARG | ASP | TRP | VAL | ASN | HIS | VAL | ARG | GLU | LYS | THR | GLY | LYS | GLU |
|     |     |     |     | 260 |     |     |     | 265 |     |     |     | 270 |
| MET | PHE | THR | VAL | ALA | GLU | TYR | TRP | GLN | ASN | ASP | LEU | GLY | ALA | LEU |
|     |     |     |     | 275 |     |     |     | 280 |     |     |     | 285 |
| GLU | ASN | TYR | LEU | ASN | LYS | THR | ASN | PHE | ASN | HIS | SER | VAL | PHE | ASP |
|     |     |     |     | 290 |     |     |     | 295 |     |     |     | 300 |
| VAL | PRO | LEU | HIS | TYR | GLN | PHE | HIS | ALA | ALA | SER | THR | GLN | GLY | GLY |
|     |     |     |     | 305 |     |     |     | 310 |     |     |     | 315 |
| GLY | TYR | ASP | MET | ARG | LYS | LEU | LEU | ASN | GLY | THR | VAL | VAL | SER | LYS |
|     |     |     |     | 320 |     |     |     | 325 |     |     |     | 330 |
| HIS | PRO | LEU | LYS | SER | VAL | THR | PHE | VAL | ASP | ASN | HIS | ASP | THR | GLN |
|     |     |     |     | 335 |     |     |     | 340 |     |     |     | 345 |
| PRO | GLY | GLN | SER | LEU | GLU | SER | THR | VAL | GLN | THR | TRP | PHE | LYS | PRO |

FIG._1A

```
                           350                 355                 360
LEU ALA TYR ALA PHE ILE LEU THR ARG GLU SER GLY TYR PRO GLN
                   365                 370                 375
VAL PHE TYR GLY ASP MET TYR GLY THR LYS GLY ASP SER GLN ARG
                   380                 385                 390
GLU ILE PRO ALA LEU LYS HIS LYS ILE GLU PRO ILE LEU LYS ALA
                   395                 400                 405
ARG LYS GLN TYR ALA TYR GLY ALA GLN HIS ASP TYR PHE ASP HIS
                   410                 415                 420
HIS ASP ILE VAL GLY TRP THR ARG GLU GLY ASP SER SER VAL ALA
                   425                 430                 435
ASN SER GLY LEU ALA ALA LEU ILE THR ASP GLY PRO GLY GLY ALA
                   440                 445                 450
LYS ARG MET TYR VAL GLY ARG GLN ASN ALA GLY GLU THR TRP HIS
                   455                 460                 465
ASP ILE THR GLY ASN ARG SER GLU PRO VAL VAL ILE ASN SER GLU
                   470                 475                 480
GLY TRP GLY GLU PHE HIS VAL ASN GLY GLY SER VAL SER ILE TYR
               483
    VAL GLN ARG
```

AMYLOLYTIC ENZYMES DERIVED FROM THE B.LICHENIFORMIS α-AMYLASE, HAVING IMPROVED CHARACTERISTICS

This is a continuation of application Ser. No. 08/981,184, filed Dec. 11, 1997 now abandoned.

The present invention relates to amylolytic enzymes, particularly α-amylases which are derived from such enzymes as present in *Bacillus licheniformis*.

α-Amylases hydrolyse starch, glycogen and related polysaccharides by cleaving internal α-1,4-glucosidic bonds at random.

Starch consists of a mixture of amylose (15–30% w/w) and amylopectin (70–85% w/w). Amylose consists of linear chains of α-1,4-linked glucose units having a molecular weight (MW) from about 60,000 to about 800,000. Amylopectin is a branched polymer containing α-1,6 branch points every 24–30 glucose units, its MW may be as high as 100 million.

Starch and especially derivatized starch or thinned starch are important for a number of technical applications, e.g. as substrate for sugar and alcohol production, as an intermediate in polymer production or as technical aid during the production of textiles and paper. Starch is also the major component of stains derived from e.g. chocolate, pap or porridge on clothes and dishes.

Thinning of starch, also called liquefaction, is a first step which is necessary in most applications of starch mentioned above. This thinning step can be very conveniently carried out using α-amylase.

The α-amylase used thus far are isolated from a wide variety of bacterial, fungal, plant and animal sources. The industrially most commonly used amylases are those isolated from *Bacilli*.

A known drawback of enzymatic reactions is that enzymes are active over a quite limited range of conditions such as pH, ionic strength and especially temperature.

The α-amylase from *B.licheniformis* is one of the most stable ones in that last respect known so far and is therefore used in applications where the thermostability of the enzyme is crucial. However, the stability of this enzyme depends on the calcium concentration in the application and the optimum activity is observed at neutral pH. A more thermostable variant of the *B.licheniformis* enzyme, which has the same specific activity as the wild type enzyme, has been described in PCT/EP90/01042.

It has been shown in PCT/DK93/00230 that it is possible to improve the oxidation stability of *B.licheniformis* α-amylase by replacing methionines by one of the other 19 possible amino acids. In the specified test under the given conditions one of these mutants showed a slightly higher activity level than the wild type enzyme.

Though it has been shown that it is possible to improve the stability of amylolytic enzymes, in particular α-amylase, for some detrimental conditions, there is as yet no α-amylase available which has the same or better activity under suboptimal conditions than the wild type enzyme at optimum conditions. Suboptimal conditions are herein defined as conditions which use a pH other than neutral, e.g. lower than 6.5 or higher than 7.5, and/or conditions which use a lower than optimal $Ca^{2+}$ concentration, i.e. lower than 50 ppm.

Because in most industrial applications the conditions are at best suboptimal, the problem of diminished activity could be solved by providing an enzyme which, at optimum conditions, has a higher activity than the wild type enzyme It would then still have sufficient activity at sub-optimal conditions. The invention provides exactly such enzymes.

The invention provides an amylolytic enzyme derived from the amylolytic enzyme of *Bacillus licheniformis* or an enzyme having at least 70%, or preferably at least 90%, amino acid identity therewith which comprises at least one change of an amino acid in its sequence to another amino acid which provides the enzyme with a higher activity than the wild type enzyme. The activity of an amylolytic enzyme is herein defined as the specific activity as determined in Example 2. The higher activity of the mutant enzymes is apparent under optimal conditions but also under suboptimal conditions where a pH value of less than pH 6.5 or higher than pH 7.5 and/or a $Ca^{2+}$ concentration of less then 50 ppm is used. In addition, the invention provides such amylolytic enzymes with a higher thermostability than the wild-type enzyme, wherein the thermostability is defined as determined in Example 3. For some of the mutant enzymes, the improved thermostability is most pronounced under suboptimal conditions regarding the $Ca^{2+}$ concentration.

Figure 1B:
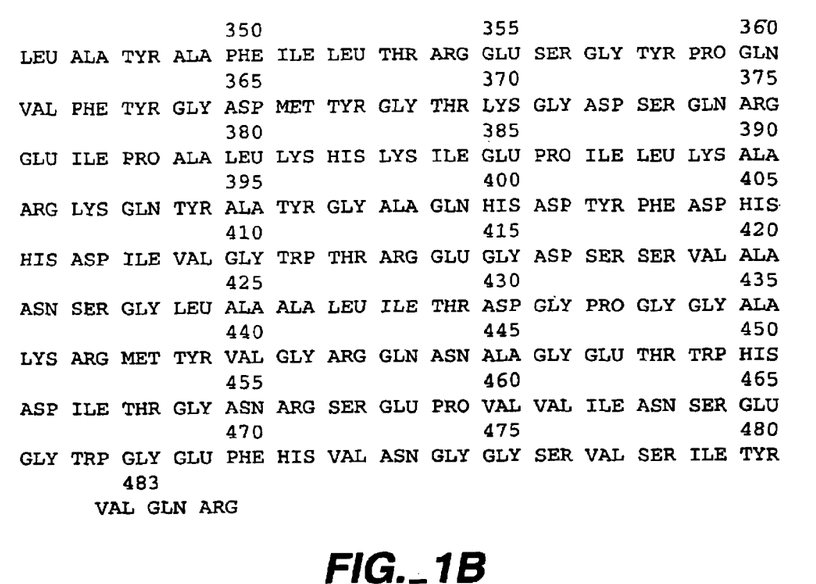
FIG. 1 gives the amino acid sequence of the α-amylase of *B. licheniformis* (SEQ ID NO: 2). The numbers relate to the positions of the amino acids given in the sequence. They are used to identify the mutations, which are gibe in one letter amino acid code in the text of the application.

The amino acid sequence of the *B.licheniformis* α-amylase is shown in FIG. 1. The numbers indicate the position of an amino acid in the sequence and will be used as an indication for the amino acid position in the description of the amino acid changes. Regarding the corresponding amino acid changes in enzymes having at least 70%, or preferably at least 90%, amino acid identity with the *B.licheniformis* α-amylase, the skilled person will understand that the *B.licheniformis* α-amylase amino acid positions used herein refer to the corresponding conserved amino acids in the amino acid sequence of these related enzymes and not necessarily to their amino acid positions in those enzymes. It is also to be understood that these corresponding conserved amino acids are not necessarily identical to those of the *B.licheniformis* α-amylase.

In a site directed mutagenesis study we identified mutants on the amino acid sequence which influence the activity level of the enzyme. Among others, we made the following mutations: N104D, S187D, V128E and N188D, which are preferred mutant enzymes according to the invention. Some of these mutants showed a higher overall activity than the wild type enzyme. Alternatively, some of these mutations showed improved thermostability.

Although site directed mutations in the DNA encoding the amylolytic enzymes are a preferred way of arriving at the enzymes according to the invention, the man skilled in the art will be aware that there are different ways of obtaining the enzymes according to the invention and they are therefore part of this invention.

Due to the fact that until now only 3D-structure of non bacterial α-amylases are available (e.g. L. Brady et al. Acta Cryst. B47 (1991), 527–535, H. J. Swift et al. Acta Cryst. B47 (1991), 535–544, M. Quian et al. J. Mol. Biol. 231 (1993), 785–799), it is hard to predict for the α-amylase from *B.licheniformis* whether a certain amino acid at a certain position can have any influence on the activity level of the enzyme. One normally needs a 3D-structure for making such predictions, because the spatial orientation of the amino acids determines their role in the catalytic process. Without a 3D-structure of the investigated enzyme one has to relate the results of site directed mutagenesis experiments on putative active site residues on related enzymes (see e.g. L. Holm et al. Protein Engineering 3 (1990) 181–191, M. Vihinen et al. J. Biochem. 107 (1990) 267–272, T. Nagashima et al. Biosci. Biotech. Biochem. 56 (1992) 207–210, K. Takase Eur. J. Biochem. 211 (1993) 899–902, M. Søgaard et al. J. Biol. Chem. 268 (1993) 22480–22484) via a multiple sequence alignment (see e.g. L. Holm et al. Protein Engineering 3 (1990) 181–191) to the known 3D-structures. This allows the identification of the active site residues and allows to identify residues which are conserved in all similar enzymes. One normally assumes that conserved residues are crucial for the function or structure of the enzyme. It is therefore to be expected that mutations in those sites will influence the activity of the enzyme. By making mutations in said active sites it would therefore be expected that some mutations would result in higher activity. However, in *B.licheniformis* none of the mutated residues at position 104, 128, 187 and 188 are active site residues. Only position 104 is located at the end of a conserved region and could maybe be important for the activity, but also in that particular case a correct prediction of the effect of a point mutation is nearly impossible.

Another important aspect of the invention is the finding that in a number of cases the higher active mutants were slightly less thermostable than the wild type enzyme, except at least the mutations V128E and N188D, which are more stable, or at least more thermostable, than the wild type enzyme. We therefore combined them with some earlier identified mutations which are known to stabilize the wild type enzyme. These are the mutations H133Y and T149I. These extra mutations indeed stabilized the more active mutants, but moreover they surprisingly showed an even higher activity level than the higher active mutants themselves.

In a further embodiment of the invention, the mutants of the invention are combined with mutations which improve the oxidation stability of the amylolytic enzyme. Such mutant enzymes may comprise mutations known in the art to improve the oxidation stability of amylolytic enzymes, such as e.g. mutations which replace the methionine at position 197 (see e.g. PCT/DK93/00230).

As stated before, a suitable way of arriving at the enzymes according to the invention is site directed mutagenesis of a nucleic acid, especially a DNA molecule, which comprises the coding sequence for the enzymes. The mutated nucleic acid molecules themselves are also part of the invention representing novel and inventive intermediates in producing the enzymes. Also by providing these nucleic acids in a suitable vector format (whereby a vector is meant to include any suitable vehicle for expression in a cell), it is possible to express the nucleic acid in a vast array of different hosts, including homologous and heterologous hosts, such as bacteria and/or other prokaryotes, yeasts, fungi, plant cells, insect cells or mammalian cells and or other eukaryotic host cells. These host cells which can be cultured to produce the enzymes are also part of the invention.

These cells can be cultured according to known techniques, which are all adapted to the particular kind of cell to be propagated. The isolation of the enzymes according to the invention from the culture or the culture supernatant is also known in the art.

A number of mutants will be more active (i.e. higher specific activity) and/or more stable (with respect to oxidation- and/or thermo-stability) even when only parts thereof are used. These fragments are of course within the scope of this invention. It will also be possible to design mutations based upon this invention which have hardly any influence on the activity or stability, such derivatives are also a part of this invention. Some reactive residues which are present in the amino acid sequences according to the invention may also be chemically modified without having significant influence on the activity of such an enzyme. These derivatives are also a part of the invention.

The same may be stated for the nucleic acids according to the invention, which can be modified to a certain extent without influencing the important properties of the resulting enzyme. Therefore nucleic acid sequences which share at least 70% identity, or more preferably at least 90% identity, with a coding sequence for an enzyme according to the invention or which are complementary to such a sequence are part of this invention. This is also true because based on this invention it will be possible to arrive at similar improvements in activity and/or stability in closely related enzymes such as amylolytic enzymes from *B.stearothermophilus* and *B.amyloliquefaciens*.

The novel amylolytic enzymes according to the invention may be used in all known applications of the amylolytic enzymes in the state of the art.

These applications include the use in the processing of starch, e.g. for polymer production wherein starch needs to be "thinned", the use in detergent compositions to break down stains which comprise starch or starch derivatives, the use in production of sugar or alcohol, or the use in the processing of textile or paper, in particular, the use for desizing of textile or paper, respectively.

Detergent compositions comprising the novel amylolytic enzymes are also a part of the invention. These compositions may be designed for dishwashing (either by hand or automatically), for household or industrial cleaning purposes, or for cleaning textiles. These compositions may comprise the usual additives and/or ingredients such as builders, surfactants, bleaching agents and the like.

Another preferred embodiment of the invention is the use of the enzymes in producing syrup or isosyrup from starch. Syrup and isosyrup are produced using an α-amylase according to the invention which catalyzes the liquefaction (or thinning) of the starch resulting in dextrins having an average polymerization degree of about 7–10, usually followed by saccharification of the liquefied starch resulting in a syrup with a high glucose content. Optionally the syrup can be isomerized to a dextrose/fructose mixture known as isosyrup.

The invention will now be explained in more detail through the following examples, which are intended for illustration purposes only.

EXAMPLES

SHORT DESCRIPTION OF THE FIGURES

The nomenclature used for the mutations is as follows S187D means the replacement of the serine (Ser) at position 187 against an aspartic acid (Asp). Multiple mutants are designated as follows H133Y/T149I means the replacement of histidine (His) at position 133 by tyrosine (Tyr) plus the replacement of threonine (Thr) at position 149 by isoleucine (Ile).

Example 1

Production and Purification of Wild Type and Mutant α-amylases a) Genetic Procedures All molecular genetic techniques used for *E.coli* (plasmid construction, transformation, plasmid isolation, etc.) were performed according to Maniatis et al. (Molecular Cloning, A Laboratory Manual, Cold Spring Harbor, 1989). Transformation of *B.subtilis* and plasmid isolation were performed according to Harwood et al. (Molecular Biological Methods for *Bacillus*, Chichester, 1990). *E. coli* strains containing pBHATLAT or its derivatives were grown in the presence of 100 mg/l ampicillin and 2 mg/l neomycin. *Bacillus subtilis* strains harboring pBHLAT 9-derived plasmids were cultivated in medium containing 20 mg/l neomycin.

Plasmid pBHA/C1 is a *Bacillus/E.coli* shuttle vector derived from the twin vector system pMa/c5-8 of Stanssens et al. (Nucl. Acids Res. 17 (1989): 4441–4454). A complete description of pBHA1 is given in the European Patent Application EP 414297.

Figure 2:
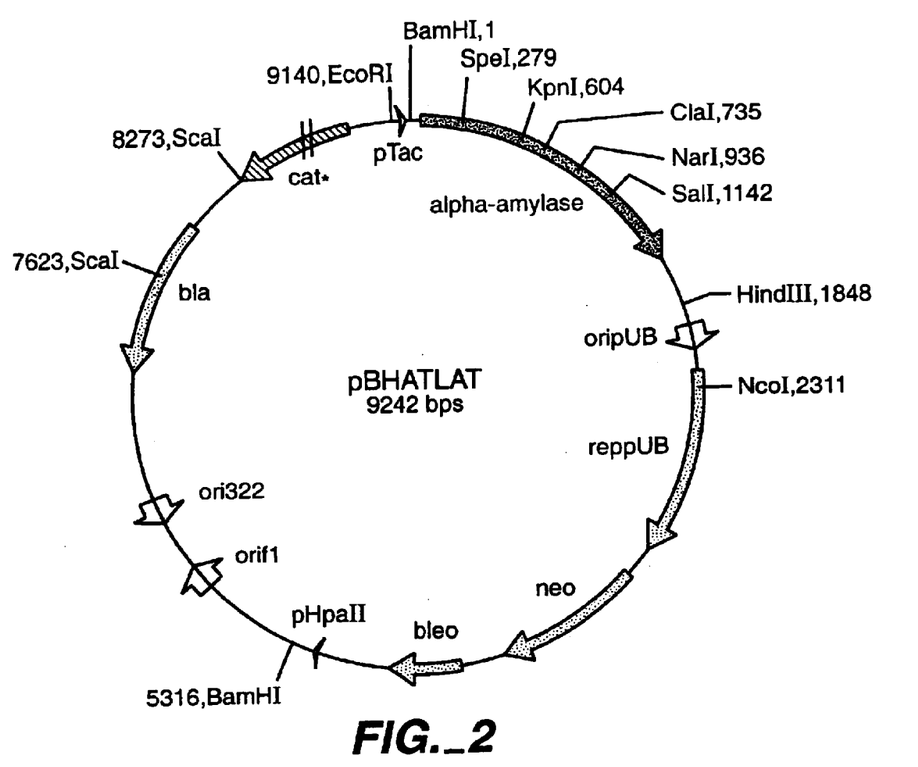
FIG. 2 gives a map of plasmid pBHATLAT. α-amylase: *B.licheniformis* α-amylase encoding gene. oripUB: origin of replication of plasmid pUB110. reppUB: replication protein of plasmid pUB110. neo: neomycin resistance gene. bleo: bleomycin resistance gene. pHpall: Hpall promoter. orifl: origin of replication of phage fl. ori322: origin of replication of plasmid pBR322. bla: β-lactamase (ampicillin resistance) gene. cat*: inactive chloramphenicol acetyl transferase (chloramphenicol resistance) gene. pTac: Tac promoter.

The *B.licheniformis* α-amylase gene used throughout this study was obtained from plasmid pMcTLia6 (WO91/00353) as an EcoRI-HinDIII restriction fragment still including the inducible Tac promoter. This fragment was inserted in EcoRI-HinDIII digested pBHA1 to yield plasmid pBHATLAT (FIG. 2). This plasmid is used for the expression of α-amylase in *E.coli* through induction of the Tac promoter by 0.2 mM IPTG. Expression of mutant α-amylase was obtained by replacing the wild type α-amylase gene fragment by the corresponding mutant gene fragment. For expression in Bacillus, plasmid pBHATLAT was digested with BamHI and subsequent relegation thus placing the α-amylase gene under the control of the constitutive Hpall promoter. Wild type and mutant α-amylase enzyme was isolated from the Bacillus culture supernatant.

Site directed mutagenesis of the α-amylase gene was performed using the PCR overlap extension technique described by Ho et al. (Gene 77 (1989): 51–59).

b) Purification of the α-amylase Wild Type and Mutants

One aliquot of the culture supernatant is added to five aliquots water of 85° C. and than maintained at 75° C. for 15 minutes. Protease activity is removed in this step. The enzyme is then isolated via ion exchange chromatography at pH 5.5 on a S-Sepharose FF column. The buffers used are 20 mM sodium acetate buffer with 1 mM CaCl$_2$ followed, with a gradient, by 20 mM sodium acetate buffer with 1 mM CaCl$_2$ and 0.5 M KCl. The pooled α-amylase fractions are concentrated by ultrafiltration via a 10 kD filter. By washing the concentrate with 1.6 mM EDTA in 50 mM MOPS, pH 7.5 the enzyme can be demetallized. Finally the concentrate is washed twice with 50 mM MOPS buffer pH 7.5.

Example 2

Determination of Activity and Enzyme Concentration

The enzyme concentration is determined by measuring the optical density at 280 nm. The extinction coefficient of wild type enzyme is 135100 M$^{-1}$ cm$^{-1}$. The mutants with the mutation H133Y have an extinction coefficient of 136430 M$^{-1}$ cm$^{-1}$. The molecular weight is 55 kD.

The α-Amylase activity is determined by means of the substrate para-Nitrophenyl-maltoheptaosoide (4NP-DP7). The reagent of Abbott (code LN5A23-22) is used. Besides 4NP-DP7 there is also α-glucosidase and glucoamylase in the substrate. α-Amylase activity is measured by the ultimate release of the chromophore p-nitrophenol (pNP).

The terminal glucose unit of the substrate is blocked with a benzylidene group. This terminal blocking inhibits cleavage by α-glucosidase until the initial bonds can be cleaved by α-amylase followed by glucoamylase. The increase of the OD405 per minute is directly proportional to the α-amylase activity.

The molar extinction coefficient of pNP at 405 nm and pH 6.8 is 7600 M$^{-1}$ cm$^{-1}$. 1 Unit is 1 μmol converted substrate per minute. With the law "Lambert-Beer" the following relationship is established:

$$\text{Activity} = \frac{OD405 * 10^6}{\epsilon^{405} * l * t} = \frac{OD405}{t} * 131.6 \left[\frac{U}{l}\right]$$

where t=time [minutes], l=lightpath [cm], $\epsilon^{405}$=molar extinction coefficient at 405 nm [M$^{-1}$*cm$^{-1}$], OD405= extinction at 405 nm, 10$^6$=calculation factor from mol/l→μmol/l Activity Assay:

Add 0.8 ml reagent solution (R1) to a bottle R2 (Abbott).

Heat the temperature controlled cuvette holder of the spectrophotometer to 37° C.

Heat the activity buffer to 37° C. (50 mM MOPS+50 mM NaCl+2 mM CaCl$_2$, pH 6.8).

Add to the cuvette in the cuvette holder: 500 μl reagent x μl sample 500—x μl activity buffer Measure the increase in extinction at 405 nm during 2 minutes.

Calculate the activity by using the above equation.

TABLE 1

Specific activities of wild type (WT) and mutant α-amylases

| Enzyme | Specific Activity [Units/mg] |
|---|---|
| wild type | 60 |
| H133Y | 52 |
| H133Y/T149I | 60 |
| N104D | 30 |
| N104D/H133Y | 46 |
| N104D/H133Y/T149I | 52 |
| V128E/H133Y | 62 |
| V128E/H133Y/T149I | 54 |
| S187D | 110 |
| H133Y/S1B7D | 155 |
| H133Y/T149I/S187D | 150 |
| H133Y/N188D | 56 |
| H133Y/T149I/N188D | 52 |
| V128E/H133Y/S187D | 142 |

Example 3

Determination of Thermostability

The enzyme is incubated in an oil bath at 93° C. in closed Eppendorff micro test tubes with safety lid lock (order-No. 0030 120.086). The Calcium concentration is varied whereas the ionic strength is kept constant. The buffer has at room temperature pH 7.5 which changes at the incubation temperature to pH 7.0. A solution of ±0,25 mg/ml protein in 50 mM MOPS pH 7.5 is obtained by mixing the right amount of enzyme in 50 mM MOPS pH 7.5 with X mM CaCl$_2$+X mM K$_2$SO$_4$+100 mM MOPS pH 7.5+water. The final buffer concentration must be 50 mM and the final volume should be 500 to 1000 µl (the best is 1000 µl). The salt composition is shown on the following table:

| mM CaCl$_2$ | mM K$_2$SO$_4$ |
|---|---|
| 0 | 15 |
| 0.25 | 14.75 |
| 0.5 | 14.5 |
| 0.75 | 14.25 |
| 1 | 14 |
| 1.25 | 13.75 |
| 1.5 | 13.5 |

Example for 0.5 mM CaCl$_2$:

250.0 µl 100 mM MOPS pH 7.5

88.0 µl enzyme (1.42 mg/ml)

50.0 µl 5 mM CaCl$_2$ 72.5 µl 100 mM K$_2$SO$_4$ 39.5 µl demi water 500.0 µl total volume The enzyme solutions are incubated in the sealed tubes at 93° C. 50 µl samples are taken after 0.5, 10, 20, 30, 60, 90 and 120 minutes. The residual activity is determined with the Abbott Quickstart Amylase essay (see above). The half life time is calculated by using the fitting program GraFit (Leatherbarrow, R. J. 1990 GraFit version 2.0, Erithacus Software Ltd., Staines, UK).

TABLE 2

Half life of the WT and mutant α-amylases at different Ca$^{2+}$ concentrations

| | Ca$^{2+}$ | | | | | | |
|---|---|---|---|---|---|---|---|
| Enzyme | 0 | 0.25 | 0.5 | 0.75 | 1 | 1.25 | 1.5 |
| | | | | Half life [min] | | | |
| wild type | 4.1 | 9.2 | 15.5 | 18.1 | 22.9 | 30.3 | 29.5 |
| H133Y | nd | 12.1 | 24.2 | 33.3 | 53.3 | nd | 77.0 |
| H133Y/T149I | 1.1 | 9.2 | 21.4 | 32.8 | 40.2 | 53.6 | 53.6 |
| N104D | nd | nd | nd | nd | 7.7 | nd | nd |
| N104D/H133Y | nd | 8.4 | 11.6 | nd | 14.4 | nd | 15.4 |
| N104D/H133Y/T149I | nd | 10.2 | 13.4 | 17.5 | 19.1 | 23.1 | 20.3 |
| V128E/H133Y | nd | 15.6 | 33.9 | nd | 53.3 | 65.3 | 77.8 |
| V128E/H133Y/T149I | nd | 19.7 | 35.2 | nd | 54.7 | nd | 76.3 |
| S187D | nd | 4.0 | 6.9 | 9.3 | 12.1 | nd | 15.1 |
| H133Y/S187D | nd | 15.2 | 19.7 | 27.0 | 29.8 | 40.8 | 47.2 |
| H133Y/T149I/S187D | 1.4 | 6.0 | 12.7 | 17.6 | 20.0 | nd | nd |
| H133Y/N188D | nd | 18.2 | 36.2 | nd | 70.4 | 76.8 | 84.9 |
| H133Y/T149I/N188D | nd | 15.8 | 28.8 | nd | 62.0 | nd | 73.6 |
| V128E/H133Y/S187D | 1.9 | 7.2 | 16.9 | nd | 32.1 | nd | 36.2 | nd = not determined

Example 4

Starch Liquefaction Using a Mutant α-amylase of the Invention

The mutant enzyme was proven to be effective in starch liquefaction tests using industrially relevant conditions. It was tested under identical conditions in comparison with the wild type enzyme. A 34.3% dry solids starch slurry was liquefied using a pilot plant jet cooking apparatus, Hydroheater Model # M 103-MS, at a flow rate of 2.8 per minute. A 5 minutes retention time at 105° C. of primary liquefaction was followed by a 93° C. 120 min secondary liquefaction. The comparison tests vis a vis the wild type enzyme were performed based upon equal Modified Wohlgemuth Units (MWU) 168 units/gram of starch. The specific activity is for wild type 18,447 MWU/mg and for H133Y/S187D 48,000 MWU/mg respectively.

The enzymes were tested under two sets of conditions. The first experiment used standard industrial conditions (pH 6.4, 44 ppm Calcium), while the second experiment employed stress conditions (pH 5.8, 8 ppm Calcium).

The decrease in viscosity during liquefaction was measured with a #3 Zahn cup, while Dextrose Equivalent (DE) development was measured using a reducing sugar assay. The results are summarized in the following tables:

TABLE 3

Experiment 1: pH 6.4, 44 ppm Calcium

| | Wild type | | H133Y/S187D | |
|---|---|---|---|---|
| time (min) | DE | Viscosity | DE | Viscosity |
| 0 | | 25 | | 24 |
| 20 | 2.7 | | 2.4 | |
| 40 | 4.0 | | 3.5 | |
| 60 | 5.4 | 14 | 4.7 | 14 |
| 80 | 6.5 | | 6.0 | |
| 100 | 7.8 | | 7.5 | |
| 120 | 9.2 | 12 | 8.8 | 12 |

TABLE 4

Experiment 2: pH 5.8, 8 ppm Calcium

| | Wild type | | H133Y/S187D | |
|---|---|---|---|---|
| time (min) | DE | Viscosity | DE | Viscosity |
| 0 | | 36 | | 38 |
| 20 | 0.3 | | 1.1 | |
| 40 | 1.1 | | 2.0 | |
| 60 | 2.0 | 17 | 2.9 | 15 |
| 80 | 2.5 | | 3.5 | |
| 100 | 3.2 | | 4.2 | |
| 120 | 3.9 | 13 | 4.6 | 13 |

Example 5

Textile Desizing Using a Mutant α-amylase of the Invention

Cretonne cotton patches (30*30 cm, J. Hacot et Cie., 48 Rue Mermoz, La Gorgue, France) are impregnated with 12% soluble starch (weight/weight) as sizing agent. The sized cotton is given in a beaker with one liter tap water and 0.5 ml/l wetting agent at 25° C. and pH 7.0. α-Amylase is added in a concentration as shown in the table. The mixture is agitated and heated with a gradient of 2° C. per minute within 30 minutes to a final temperature of 85° C. After 10 minutes agitating at the final temperature the fabric is 2 minutes rinsed with cold water and dried.

The residual starch is determined with a reflectrometric method. The residual starch on the fibres is coloured with a solution made from 0.15 g iodine, 0.5 g potassium iodine and 10 ml 2 N H$_2$SO$_4$ in a volume of 1 l water. The dried cotton patch is wetted with alcohol and soaked in the colouring solution for 15 minutes. The reflectance of the coloured patch is measured at 700 nm with a Universal Messeinheit UME 1 III/LR 90 reflectometer (Dr. Bruno Lange GmbH, Berlin, Germany). The amount of residual starch can be calculated with a calibration curve recorded with known amounts of starch on the fabric.

TABLE 5

A comparison of the performance of the wild type and a mutant α-amylase in the desizing of textile.

| wild type | | H133Y/S187D | |
|---|---|---|---|
| enzyme concentration [μmol/l] | remaining starch on fabrics [mg/g] | enzyme concentration [μmol/l] | remaining starch on fabric [mg/g] |
| 0 | 3.92 | 0 | 4.05 |
| 9.3 | 3.35 | 2.5 | 3.35 |
| 18.5 | 2.76 | 4.9 | 2.45 |
| 37.2 | 2.25 | 7.6 | 2.02 |
| 46.5 | 1.85 | 9.1 | 1.72 |
| 70 | 1.42 | 12.5 | 1.37 |
| 93 | 0.9 | 18.9 | 1.12 |
| | | 25.3 | 0.68 |
| | | 37.8 | 0.5 |

Example 6

A Comparison of the Wash Performance of the Wild Type and a Mutant α-amylase

The wash performance of the wild type vis a vis the H133Y/S187D mutant was tested in a full scale wash experiment using the amylase sensitive cotton test fabric EMPA 112 as monitor. In all tests the α-amylase dosage was 1.3 mg/l suds. A blank was taken as reference. Washing powder base was the IEC reference detergent A, containing bleach and protease. All tests were carried out in quintuple. The fabrics were washed in a Miele, type W701 washing machine at 40° C. and a total load of 4 kg fabrics. The soil removal was determined by measuring the white light reflection with a Colorgard Model 05 (Gardner Lab., USA) reflectometer. Table summarizes the results. It shows that the mutant performs better than wild type enzyme at the same dosage.

TABLE 6

A comparison of the wash performance of the wild type and a mutant α-amylase

| Enzyme | none | wild type | H133Y/S187D |
|---|---|---|---|
| Soil removal | 31.7% | 40.2% | 42.1% |

---

What is claimed is:

1. An amylolytic enzyme derived from an α-amylase of *Bacillus licheniformis* having SEQ ID NO: 2 which comprises one or more amino acid changes at positions selected from the group consisting of positions 104, 128, 187 and 188 of the amino acid sequence of the an α-amylase of *Bacillus licheniformis*.

2. A mutant amylolytic enzyme derived from an α-amylase of a *Bacillus* comprising a substitution of an amino acid residue at a position corresponding to positions in the amino acid sequence of SEQ ID NO: 2 selected from the group consisting of Asn at position 104 to Asp, Val at position 128 to Glu, Ser at position 187 to Asp, and Asn at position 188 to Asp.

3. An isolated nucleic acid molecule encoding an enzyme according to claim 2.

4. A vector for expression of an enzyme, comprising a nucleic acid according to claim 3, together with suitable elements for expression.

5. A cell for expressing an enzyme, comprising a nucleic acid molecule or a vector according to claim 3 or claim 4.

6. A process for producing an enzyme, which comprises culturing a cell according to claim 5 in a suitable medium for expression of said enzyme and after a suitable amount of time isolating the enzyme from the culture.

7. A detergent composition comprising an enzyme according to claim 2.

8. The mutant amylolytic enzyme of claim 2, wherein the substitution is Asn at position 104 to Asp.

9. The mutant amylolytic enzyme of claim 2, wherein the substitution is Val at position 128 to Glu.

10. The mutant amylolytic enzyme of claim 2, wherein the substitution is Asn at position 188 to Asp.

11. The mutant amylolytic enzyme of claim 2, further comprising a substitution of His to Tyr at a position corresponding to position 133 in the amino acid sequence of SEQ ID NO: 2.

12. The mutant amylolytic enzyme of claim 2, further comprising a substitution of Met at a position corresponding to position 197 in the amino acid sequence of SEQ ID NO: 2.

13. A mutant amylolytic enzyme derived from an α-amylase of a *Bacillus* comprising a substitution of an amino acid residue corresponding to Asn at position 104 in the amino acid sequence of SEQ ID NO: 2.

14. A mutant amylolytic enzyme derived from an α-amylase of a *Bacillus* comprising a substitution of an amino acid residue corresponding to Ser at position 187 in the amino acid sequence of SEQ ID NO: 2.

15. The mutant amylolytic of claim 14, wherein the substitution is Ser to Asp at a position corresponding to position 187 in the amino acid sequence of SEQ ID NO: 2.

16. The mutant amylolytic enzyme of claim 14 further comprising an amino acid substitution of His to Tyr at a position corresponding to position 133 in the amino acid sequence of SEQ ID NO: 2.

17. The mutant amylolytic enzyme of claim 14 further comprising an amino acid substitution of Val to Glu at position corresponding to position 128 in the amino acid sequence of SEQ ID NO: 2.

18. A detergent composition comprising the mutant amylolytic enzyme of claim 14.

19. A mutant amylolytic enzyme derived from an α-amylase of a *Bacillus* comprising a substitution of (a) His to Tyr at a position corresponding to position 133 and (b) Ser to Asp at a position corresponding to position 187 in the amino acid sequence of SEQ ID NO: 2.

20. The mutant amylolytic enzyme of claim 19 further comprising an amino acid substitution of Val to Glu at a position corresponding to position 128 in the amino acid sequence of SEQ ID NO: 2.

21. The mutant amylolytic enzyme of claim 19 further comprising an amino acid substitution of Thr to Ile at a position corresponding to position 149 in the amino acid sequence of SEQ ID NO: 2.

22. A detergent composition comprising the amylolytic enzyme of claim 21.

* * * * *

SEQUENCE LISTING

<160> NUMBER OF SEQ ID NOS: 3

<210> SEQ ID NO 1
<211> LENGTH: 1539
<212> TYPE: DNA
<213> ORGANISM: Bacillus licheniformis
<220> FEATURE:
<221> NAME/KEY: CDS
<222> LOCATION: (1)...(1539)
<220> FEATURE:
<221> NAME/KEY: sig_peptide
<222> LOCATION: (1)...(87)
<220> FEATURE:
<221> NAME/KEY: mat_peptide
<222> LOCATION: (88)...(1539)
<223> OTHER INFORMATION: alpha-amylase

<400> SEQUENCE: 1

```
atg aaa caa caa aaa cgg ctt tac gcc cga ttg ctg acg ctg tta ttt      48
Met Lys Gln Gln Lys Arg Leu Tyr Ala Arg Leu Leu Thr Leu Leu Phe
            -25                 -20                 -15 gcg ctc atc ttc ttg ctg cct cat tct gca gca gcg gcg aat ctt           96
Ala Leu Ile Phe Leu Leu Pro His Ser Ala Ala Ala Ala Asn Leu
        -10                  -5                   1 aat ggg acg ctg atg cag tat ttt gaa tgg tac atg ccc aat gac ggc     144
Asn Gly Thr Leu Met Gln Tyr Phe Glu Trp Tyr Met Pro Asn Asp Gly
  5                  10                  15 caa cat tgg aag cgt ttg caa aac gac tcg gca tat ttg gct gaa cac     192
Gln His Trp Lys Arg Leu Gln Asn Asp Ser Ala Tyr Leu Ala Glu His
 20                  25                  30                  35 ggt att act gcc gtc tgg att ccc ccg gca tat aag gga act agt caa     240
Gly Ile Thr Ala Val Trp Ile Pro Pro Ala Tyr Lys Gly Thr Ser Gln
         40                  45                  50
```

-continued

```
gcg gat gtg ggc tac ggt gct tac gac ctt tat gat tta ggg gag ttt      288
Ala Asp Val Gly Tyr Gly Ala Tyr Asp Leu Tyr Asp Leu Gly Glu Phe
            55                  60                  65 cat caa aaa ggg acg gtt cgg aca aag tac ggc aca aaa gga gag ctg      336
His Gln Lys Gly Thr Val Arg Thr Lys Tyr Gly Thr Lys Gly Glu Leu
        70                  75                  80 caa tct gcg atc aaa agt ctt cat tcc cgc gac att aac gtt tac ggg      384
Gln Ser Ala Ile Lys Ser Leu His Ser Arg Asp Ile Asn Val Tyr Gly
    85                  90                  95 gat gtg gtc atc aac cac aaa ggc ggc gct gat gcg acc gaa gat gta      432
Asp Val Val Ile Asn His Lys Gly Gly Ala Asp Ala Thr Glu Asp Val
100                 105                 110                 115 acc gcg gtt gaa gtc gat ccc gct gac cgc aac cgc gta att tca gga      480
Thr Ala Val Glu Val Asp Pro Ala Asp Arg Asn Arg Val Ile Ser Gly
                120                 125                 130 gaa cac cta att aaa gcc tgg aca cat ttt cat ttt ccg ggg cgc ggc      528
Glu His Leu Ile Lys Ala Trp Thr His Phe His Phe Pro Gly Arg Gly
            135                 140                 145 agc aca tac agc gat ttt aaa tgg cat tgg tac cat ttt gac gga acc      576
Ser Thr Tyr Ser Asp Phe Lys Trp His Trp Tyr His Phe Asp Gly Thr
        150                 155                 160 gat tgg gac gag tcc cga aag ctg aac cgc atc tat aag ttt caa gga      624
Asp Trp Asp Glu Ser Arg Lys Leu Asn Arg Ile Tyr Lys Phe Gln Gly
165                 170                 175 aag gct tgg gat tgg gaa gtt tcc aat gaa aac ggc aac tat gat tat      672
Lys Ala Trp Asp Trp Glu Val Ser Asn Glu Asn Gly Asn Tyr Asp Tyr
180                 185                 190                 195 ttg atg tat gcc gac atc gat tat gac cat cct gat gtc gca gca gaa      720
Leu Met Tyr Ala Asp Ile Asp Tyr Asp His Pro Asp Val Ala Ala Glu
                200                 205                 210 att aag aga tgg ggc act tgg tat gcc aat gaa ctg caa ttg gac ggt      768
Ile Lys Arg Trp Gly Thr Trp Tyr Ala Asn Glu Leu Gln Leu Asp Gly
            215                 220                 225 ttc cgt ctt gat gct gtc aaa cac att aaa ttt tct ttt ttg cgg gat      816
Phe Arg Leu Asp Ala Val Lys His Ile Lys Phe Ser Phe Leu Arg Asp
        230                 235                 240 tgg gtt aat cat gtc agg gaa aaa acg ggg aag gaa atg ttt acg gta      864
Trp Val Asn His Val Arg Glu Lys Thr Gly Lys Glu Met Phe Thr Val
    245                 250                 255 gct gaa tat tgg cag aat gac ttg ggc gcc ctg gaa aac tat ttg aac      912
Ala Glu Tyr Trp Gln Asn Asp Leu Gly Ala Leu Glu Asn Tyr Leu Asn
260                 265                 270                 275 aaa aca aat ttt aat cat tca gtg ttt gac gtg ccg ctt cat tat cag      960
Lys Thr Asn Phe Asn His Ser Val Phe Asp Val Pro Leu His Tyr Gln
                280                 285                 290 ttc cat gct gca tcg aca cag gga ggc ggc tat gat atg agg aaa ttg     1008
Phe His Ala Ala Ser Thr Gln Gly Gly Gly Tyr Asp Met Arg Lys Leu
            295                 300                 305 ctg aac ggt acg gtc gtt tcc aag cat ccg ttg aaa tcg gtt aca ttt     1056
Leu Asn Gly Thr Val Val Ser Lys His Pro Leu Lys Ser Val Thr Phe
        310                 315                 320 gtc gat aac cat gat aca cag ccg ggg caa tcg ctt gag tcg act gtc     1104
Val Asp Asn His Asp Thr Gln Pro Gly Gln Ser Leu Glu Ser Thr Val
    325                 330                 335 caa aca tgg ttt aag ccg ctt gct tac gct ttt att ctc aca agg gaa     1152
Gln Thr Trp Phe Lys Pro Leu Ala Tyr Ala Phe Ile Leu Thr Arg Glu
340                 345                 350                 355
```

-continued

```
tct gga tac cct cag gtt ttc tac ggg gat atg tac ggg acg aaa gga      1200
Ser Gly Tyr Pro Gln Val Phe Tyr Gly Asp Met Tyr Gly Thr Lys Gly
            360                 365                 370 gac tcc cag cgc gaa att cct gcc ttg aaa cac aaa att gaa ccg atc      1248
Asp Ser Gln Arg Glu Ile Pro Ala Leu Lys His Lys Ile Glu Pro Ile
        375                 380                 385 tta aaa gcg aga aaa cag tat gcg tac gga gca cag cat gat tat ttc      1296
Leu Lys Ala Arg Lys Gln Tyr Ala Tyr Gly Ala Gln His Asp Tyr Phe
    390                 395                 400 gac cac cat gac att gtc ggc tgg aca agg gaa ggc gac agc tcg gtt      1344
Asp His His Asp Ile Val Gly Trp Thr Arg Glu Gly Asp Ser Ser Val
405                 410                 415 gca aat tca ggt ttg gcg gca tta ata aca gac gga ccc ggt ggg gca      1392
Ala Asn Ser Gly Leu Ala Ala Leu Ile Thr Asp Gly Pro Gly Gly Ala
420                 425                 430                 435 aag cga atg tat gtc ggc cgg caa aac gcc ggt gag aca tgg cat gac      1440
Lys Arg Met Tyr Val Gly Arg Gln Asn Ala Gly Glu Thr Trp His Asp
                440                 445                 450 att acc gga aac cgt tcg gag ccg gtt gtc atc aat tcg gaa ggc tgg      1488
Ile Thr Gly Asn Arg Ser Glu Pro Val Val Ile Asn Ser Glu Gly Trp
            455                 460                 465 gga gag ttt cac gta aac ggc ggg tcg gtt tca att tat gtt caa aga      1536
Gly Glu Phe His Val Asn Gly Gly Ser Val Ser Ile Tyr Val Gln Arg
        470                 475                 480 tag                                                                   1539
```

<210> SEQ ID NO 2
<211> LENGTH: 512
<212> TYPE: PRT
<213> ORGANISM: Bacillus licheniformis

<400> SEQUENCE: 2

```
Met Lys Gln Gln Lys Arg Leu Tyr Ala Arg Leu Leu Thr Leu Leu Phe
  1               5                  10                  15

Ala Leu Ile Phe Leu Leu Pro His Ser Ala Ala Ala Ala Ala Asn Leu
                20                  25                  30

Asn Gly Thr Leu Met Gln Tyr Phe Glu Trp Tyr Met Pro Asn Asp Gly
            35                  40                  45

Gln His Trp Lys Arg Leu Gln Asn Asp Ser Ala Tyr Leu Ala Glu His
        50                  55                  60

Gly Ile Thr Ala Val Trp Ile Pro Pro Ala Tyr Lys Gly Thr Ser Gln
 65                  70                  75                  80

Ala Asp Val Gly Tyr Gly Ala Tyr Asp Leu Tyr Asp Leu Gly Glu Phe
                 85                  90                  95

His Gln Lys Gly Thr Val Arg Thr Lys Tyr Gly Thr Lys Gly Glu Leu
            100                 105                 110

Gln Ser Ala Ile Lys Ser Leu His Ser Arg Asp Ile Asn Val Tyr Gly
        115                 120                 125

Asp Val Val Ile Asn His Lys Gly Gly Ala Asp Ala Thr Glu Asp Val
    130                 135                 140

Thr Ala Val Glu Val Asp Pro Ala Asp Arg Asn Arg Val Ile Ser Gly
145                 150                 155                 160

Glu His Leu Ile Lys Ala Trp Thr His Phe His Phe Pro Gly Arg Gly
                165                 170                 175

Ser Thr Tyr Ser Asp Phe Lys Trp His Trp Tyr His Phe Asp Gly Thr
            180                 185                 190
```

```
Asp Trp Asp Glu Ser Arg Lys Leu Asn Arg Ile Tyr Lys Phe Gln Gly
            195                 200                 205

Lys Ala Trp Asp Trp Glu Val Ser Asn Glu Asn Gly Asn Tyr Asp Tyr
        210                 215                 220

Leu Met Tyr Ala Asp Ile Asp Tyr Asp His Pro Asp Val Ala Ala Glu
225                 230                 235                 240

Ile Lys Arg Trp Gly Thr Trp Tyr Ala Asn Glu Leu Gln Leu Asp Gly
                245                 250                 255

Phe Arg Leu Asp Ala Val Lys His Ile Lys Phe Ser Phe Leu Arg Asp
            260                 265                 270

Trp Val Asn His Val Arg Glu Lys Thr Gly Lys Glu Met Phe Thr Val
        275                 280                 285

Ala Glu Tyr Trp Gln Asn Asp Leu Gly Ala Leu Glu Asn Tyr Leu Asn
290                 295                 300

Lys Thr Asn Phe Asn His Ser Val Phe Asp Val Pro Leu His Tyr Gln
305                 310                 315                 320

Phe His Ala Ala Ser Thr Gln Gly Gly Gly Tyr Asp Met Arg Lys Leu
                325                 330                 335

Leu Asn Gly Thr Val Val Ser Lys His Pro Leu Lys Ser Val Thr Phe
            340                 345                 350

Val Asp Asn His Asp Thr Gln Pro Gly Gln Ser Leu Glu Ser Thr Val
        355                 360                 365

Gln Thr Trp Phe Lys Pro Leu Ala Tyr Ala Phe Ile Leu Thr Arg Glu
370                 375                 380

Ser Gly Tyr Pro Gln Val Phe Tyr Gly Asp Met Tyr Gly Thr Lys Gly
385                 390                 395                 400

Asp Ser Gln Arg Glu Ile Pro Ala Leu Lys His Lys Ile Glu Pro Ile
                405                 410                 415

Leu Lys Ala Arg Lys Gln Tyr Ala Tyr Gly Ala Gln His Asp Tyr Phe
            420                 425                 430

Asp His His Asp Ile Val Gly Trp Thr Arg Glu Gly Asp Ser Ser Val
        435                 440                 445

Ala Asn Ser Gly Leu Ala Ala Leu Ile Thr Asp Gly Pro Gly Gly Ala
450                 455                 460

Lys Arg Met Tyr Val Gly Arg Gln Asn Ala Gly Glu Thr Trp His Asp
465                 470                 475                 480

Ile Thr Gly Asn Arg Ser Glu Pro Val Val Ile Asn Ser Glu Gly Trp
                485                 490                 495

Gly Glu Phe His Val Asn Gly Gly Ser Val Ser Ile Tyr Val Gln Arg
            500                 505                 510
```

<210> SEQ ID NO 3
<211> LENGTH: 483
<212> TYPE: PRT
<213> ORGANISM: Bacillus licheniformis

<400> SEQUENCE: 3

```
Ala Asn Leu Asn Gly Thr Leu Met Gln Tyr Phe Glu Trp Tyr Met Pro
1               5                   10                  15

Asn Asp Gly Gln His Trp Lys Arg Leu Gln Asn Asp Ser Ala Tyr Leu
            20                  25                  30

Ala Glu His Gly Ile Thr Ala Val Trp Ile Pro Pro Ala Tyr Lys Gly
        35                  40                  45

Thr Ser Gln Ala Asp Val Gly Tyr Gly Ala Tyr Asp Leu Tyr Asp Leu
    50                  55                  60
```

-continued

```
Gly Glu Phe His Gln Lys Gly Thr Val Arg Thr Lys Tyr Gly Thr Lys
 65                  70                  75                  80

Gly Glu Leu Gln Ser Ala Ile Lys Ser Leu His Ser Arg Asp Ile Asn
                 85                  90                  95

Val Tyr Gly Asp Val Val Ile Asn His Lys Gly Gly Ala Asp Ala Thr
            100                 105                 110

Glu Asp Val Thr Ala Val Glu Val Asp Pro Ala Asp Arg Asn Arg Val
        115                 120                 125

Ile Ser Gly Glu His Leu Ile Lys Ala Trp Thr His Phe His Phe Pro
130                 135                 140

Gly Arg Gly Ser Thr Tyr Ser Asp Phe Lys Trp His Trp Tyr His Phe
145                 150                 155                 160

Asp Gly Thr Asp Trp Asp Glu Ser Arg Lys Leu Asn Arg Ile Tyr Lys
                165                 170                 175

Phe Gln Gly Lys Ala Trp Asp Trp Glu Val Ser Asn Glu Asn Gly Asn
            180                 185                 190

Tyr Asp Tyr Leu Met Tyr Ala Asp Ile Asp Tyr Asp His Pro Asp Val
        195                 200                 205

Ala Ala Glu Ile Lys Arg Trp Gly Thr Trp Tyr Ala Asn Glu Leu Gln
210                 215                 220

Leu Asp Gly Phe Arg Leu Asp Ala Val Lys His Ile Lys Phe Ser Phe
225                 230                 235                 240

Leu Arg Asp Trp Val Asn His Val Arg Glu Lys Thr Gly Lys Glu Met
                245                 250                 255

Phe Thr Val Ala Glu Tyr Trp Gln Asn Asp Leu Gly Ala Leu Glu Asn
            260                 265                 270

Tyr Leu Asn Lys Thr Asn Phe Asn His Ser Val Phe Asp Val Pro Leu
        275                 280                 285

His Tyr Gln Phe His Ala Ala Ser Thr Gln Gly Gly Tyr Asp Met
290                 295                 300

Arg Lys Leu Leu Asn Gly Thr Val Val Ser Lys His Pro Leu Lys Ser
305                 310                 315                 320

Val Thr Phe Val Asp Asn His Asp Thr Gln Pro Gly Gln Ser Leu Glu
                325                 330                 335

Ser Thr Val Gln Thr Trp Phe Lys Pro Leu Ala Tyr Ala Phe Ile Leu
            340                 345                 350

Thr Arg Glu Ser Gly Tyr Pro Gln Val Phe Tyr Gly Asp Met Tyr Gly
        355                 360                 365

Thr Lys Gly Asp Ser Gln Arg Glu Ile Pro Ala Leu Lys His Lys Ile
370                 375                 380

Glu Pro Ile Leu Lys Ala Arg Lys Gln Tyr Ala Tyr Gly Ala Gln His
385                 390                 395                 400

Asp Tyr Phe Asp His His Asp Ile Val Gly Trp Thr Arg Glu Gly Asp
                405                 410                 415

Ser Ser Val Ala Asn Ser Gly Leu Ala Ala Leu Ile Thr Asp Gly Pro
            420                 425                 430

Gly Gly Ala Lys Arg Met Tyr Val Gly Arg Gln Asn Ala Gly Glu Thr
        435                 440                 445
```

-continued

```
Trp His Asp Ile Thr Gly Asn Arg Ser Glu Pro Val Val Ile Asn Ser
    450                 455                 460

Glu Gly Trp Gly Glu Phe His Val Asn Gly Gly Ser Val Ser Ile Tyr
465                 470                 475                 480

Val Gln Arg
```